United States Patent
Shute et al.

(10) Patent No.: US 12,390,125 B2
(45) Date of Patent: Aug. 19, 2025

(54) ACCELERATION BASED PATIENT WEIGHT DETERMINATION

(71) Applicant: Cardiac Pacemakers, Inc., St. Paul, MN (US)

(72) Inventors: Jonathan Bennett Shute, Eagan, MN (US); Rezwan Ahmed, Arden Hills, MN (US); Gezheng Wen, Shoreview, MN (US); Pramodsingh Hirasingh Thakur, Woodbury, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 692 days.

(21) Appl. No.: 17/725,945

(22) Filed: Apr. 21, 2022

(65) Prior Publication Data

US 2022/0354384 A1    Nov. 10, 2022

Related U.S. Application Data

(60) Provisional application No. 63/185,848, filed on May 7, 2021.

(51) Int. Cl.
*A61B 5/103*     (2006.01)
*A61B 5/00*      (2006.01)
(Continued)

(52) U.S. Cl.
CPC .......... *A61B 5/1038* (2013.01); *A61B 5/0031* (2013.01); *A61B 5/0537* (2013.01);
(Continued)

(58) Field of Classification Search
CPC ... A61B 5/1038; A61B 5/0031; A61B 5/0537; A61B 5/112; A61B 5/1126;
(Continued)

(56) References Cited

U.S. PATENT DOCUMENTS 9,622,664 B2    4/2017  An et al.
9,968,266 B2    5/2018  An et al.
(Continued)

FOREIGN PATENT DOCUMENTS

CN    117279569 A    12/2023
JP    2011008612 A    1/2011
(Continued)

OTHER PUBLICATIONS

"European Application Serial No. 22722054.8, Response filed May 31, 2024 to Communication Pursuant to Rules 161(1) and 162 EPC", 18 pgs.

(Continued)

*Primary Examiner* — Sean A Frith
(74) *Attorney, Agent, or Firm* — Schwegman Lundberg & Woessner, P.A.

(57) ABSTRACT

Systems and methods are disclosed to determine a measure of patient weight using existing medical device sensors, comprising receiving acceleration information of a patient and, if a value of the acceleration information exceeds an activity threshold over a measurement window, detecting patient steps in the measurement window using the acceleration information, determining a patient step rate over the measurement window using the detected patient steps, determining a measure of patient step force for the measurement window, and determining a measure of patient weight using the determined patient step rate and measure of patient step force.

20 Claims, 6 Drawing Sheets

(51) Int. Cl.
*A61B 5/0537* (2021.01)
*A61B 5/11* (2006.01)
*A61B 7/00* (2006.01)

(52) U.S. Cl.
CPC ............ *A61B 5/112* (2013.01); *A61B 5/1126* (2013.01); *A61B 5/4848* (2013.01); *A61B 5/4878* (2013.01); *A61B 5/686* (2013.01); *A61B 7/00* (2013.01); *A61B 2562/0219* (2013.01)

(58) Field of Classification Search
CPC ..... A61B 5/4848; A61B 5/4878; A61B 5/686; A61B 7/00; A61B 2562/0219
See application file for complete search history.

(56) References Cited

U.S. PATENT DOCUMENTS

| | | | |
|---|---|---|---|
| 10,137,265 B2 | 11/2018 | Freeman et al. | |
| 10,143,385 B2 | 12/2018 | Sweeney et al. | |
| 2005/0256545 A1* | 11/2005 | Koh | A61B 5/0245 607/17 |
| 2006/0143645 A1* | 6/2006 | Vock | A63B 71/0605 725/9 |
| 2011/0054359 A1* | 3/2011 | Sazonov | A61B 5/1118 600/595 |
| 2012/0255160 A1* | 10/2012 | Boone | A61B 5/6811 29/592 |
| 2016/0089059 A1* | 3/2016 | Hu | A61B 5/7207 600/595 |
| 2017/0000384 A1 | 1/2017 | Annegarn et al. | |

FOREIGN PATENT DOCUMENTS

| | | | |
|---|---|---|---|
| JP | 2012502752 A | | 2/2012 |
| JP | 2017207325 A | * | 11/2017 |
| JP | 2017211304 A | | 11/2017 |
| JP | 2024517273 A | | 4/2024 |
| JP | 7651730 B2 | | 3/2025 |
| WO | WO-2008023978 A1 | | 2/2008 |
| WO | WO-2022235438 A1 | | 11/2022 |

OTHER PUBLICATIONS

"International Application Serial No. PCT/US2022/025719, International Preliminary Report on Patentability mailed Nov. 16, 2023", 8 pgs.

"International Application Serial No. PCT/US2022/025719, International Search Report mailed Jul. 29, 2022", 5 pgs.

"International Application Serial No. PCT/US2022/025719, Written Opinion mailed Jul. 29, 2022", 6 pgs.

"Japanese Application Serial No. 2023-568385, Notification of Reasons for Refusal mailed Nov. 12, 2024", w/ English translation, 12 pgs.

"Japanese Application Serial No. 2023-568385, Response filed Feb. 12, 2025 to Notification of Reasons for Refusal mailed Nov. 12, 2024", w/ current English claims, 7 pgs.

"Japanese Application Serial No. 2023-568385, Voluntary Amendment filed Jan. 26, 2024", w/ English claims, 11 pgs.

Bajwa, Ravneet S., "Weigh-In-Motion System Using a MEMS Accelerometer", Technical Report No. UCB/EECS-2009-127 http://www.eecs.berkeley.edu/Pubs/TechRpts/2009/EECS-2009-127.html, Sep. 1, 2009, 54 pgs.

Hellstrom, Per, et al., "Wearable Weight Estimation System", Embedded Sensor Systems for Health (ESS H), Mälardalen University (MDH), Gurksaltargatan 9, Västerås 72218, Sweden, Procedia Computer Science 64 (2015) 146-152.

Muzaffar, Shahzad, et al., "Shoe-Integrated, Force Sensor Design for Continuous Body Weight Monitoring", Jun. 2020 • Sensors 20(12):3339; doi: 10.3390/s20123339, 22 pgs.

* cited by examiner

ACCELERATION BASED PATIENT WEIGHT DETERMINATION

CLAIM OF PRIORITY

This application claims the benefit of provisional U.S. patent application Ser. No. 63/185,848, filed on May 7, 2021, which is hereby incorporated by reference in its entirety.

TECHNICAL FIELD

This document relates generally to medical devices comprising an accelerometer and more particularly to acceleration based patient weight determination.

BACKGROUND

Implantable medical devices (IMDs), such as cardiac rhythm management (CRM) devices, can be used to monitor, detect, or treat various cardiac conditions associated with a reduced ability of a heart to sufficiently deliver blood to a body. In some cases, heart conditions may lead to rapid, irregular, or inefficient heart contractions, etc. To alleviate one or more of these conditions, various medical devices can be implanted in a patient's body to monitor heart activity or to provide electrical stimulation to optimize or control contractions of the heart.

Heart failure (HF) is a reduction in the ability of the heart to deliver enough blood to meet bodily needs. Heart failure patients commonly have enlarged heart with weakened cardiac muscles, resulting in reduced contractility and poor cardiac output of blood. Typical signs of heart failure include shortness of breath, fatigue, weakness, pulmonary congestion, edema, etc.

Sudden or steady weight gain is an indication of fluid retention or accumulation, and is often one of the first physical signs of worsening heart failure. Patients with cardiac conditions, such as heart failure, are commonly provided weight scales to monitor patient weight. Traditional weight scales require patient compliance. Traditional weight scale measurements, even when taken every day and at the same time, are often difficult to rely upon, as daily variation in clothing, patient diet, fluid intake, sleep quality, the surface underneath the scale, possible inclination or declination, etc., can significantly alter individual weight measurements. Due to such unreliability, many healthcare providers and patient care facilities have stopped providing weight scales to patients to save costs.

However, a reliable, cost-effective measure of patient weight, or sudden or gradual changes in patient weight, remains clinically valuable.

SUMMARY

Systems and methods are disclosed to determine a measure of patient weight using existing medical device sensors, comprising receiving acceleration information of a patient and, if a value of the acceleration information exceeds an activity threshold over a measurement window, detecting patient steps in the measurement window using the acceleration information, determining a patient step rate over the measurement window using the detected patient steps, determining a measure of patient step force for the measurement window, and determining a measure of patient weight using the determined patient step rate and measure of patient step force.

An example (e.g., "Example 1") of subject matter (e.g., an implantable medical device) may comprise a signal receiver circuit configured to receive acceleration information of a patient and an assessment circuit configured to determine if a value of the acceleration information exceeds an activity threshold, and, in response to the value of the acceleration information exceeding the activity threshold, to detect patient steps in a measurement window using the acceleration information and, using the detected patient steps, determine a patient step rate over the measurement window and determine a measure of patient step force for the measurement window, wherein the assessment circuit is configured to determine a measure of patient weight using the determined patient step rate and measure of patient step force.

In Example 2, the subject matter of Example 1 may optionally be configured such that the assessment circuit is configured to determine patient step rates and measures of patient step force for a plurality of respective measurement windows, bin the determined measures of patient step force into one of a set of bins according to the determined patient step rate for the respective measurement window, and determine the measure of patient weight using the determined measures of patient step force of one of the set of bins.

In Example 3, the subject matter of any one or more of Examples 1-2 may optionally be configured such that the assessment circuit is configured to determine patient step rates and measures of patient step force for the plurality of respective measurement windows over a plurality of days, to determine daily measures of patient step force for each of the set of bins having determined measures of patient step force for the respective day, and to determine the measure of patient weight using the determined daily measures of patient step force of one of the set of bins.

In Example 4, the subject matter of any one or more of Examples 1-3 may optionally be configured such that the measure of patient weight comprises a change in patient weight, and the assessment circuit is configured to determine a measure of change of the determined measures of patient step force for one of the set of bins over time and to determine the change in patient weight using the determined measure of change.

In Example 5, the subject matter of any one or more of Examples 1-4 may optionally be configured such that the assessment circuit is configured to determine at least one of: an intra-day change in patient weight using a change in determined measures of patient step force for one of the set of bins occurring over one day; a short-term change in patient weight using a change in determined measures of patient step force for one of the set of bins occurring over a first period of time comprising multiple days; or a long-term change in patient weight using a change in determined measures of patient step force for one of the set of bins occurring over a second period of time longer than the first period of time.

In Example 6, the subject matter of any one or more of Examples 1-5 may optionally be configured such that the assessment circuit is configured to bin the determined measures of patient step force into one of the set of bins according to the determined patient step rate for the respective measurement window and at least one of a time-of-day of the measurement window and a length of the measurement window, and to determine the measure of patient weight using the determined measures of patient step force of one of the set of bins corresponding to at least one of a specified time-of-day or a specified length of the measurement window.

In Example 7, the subject matter of any one or more of Examples 1-6 may optionally be configured such that the set of bins correspond to different ranges of patient step rates and periods of the day, comprising: a first bin corresponding to a first range of patient step rates and a first period of the day and a first length of the measurement window; and at least one of: a second bin corresponding to the first range of patient step rates and the first period of the day and a second length of the measurement window; a third bin corresponding to the first range of patient step rates and a second period of the day and the first length of the measurement window; a fourth bin corresponding to a second range of patient step rates and the first period of the day and the first length of the measurement window; a fifth bin corresponding to the first range of patient step rates and the second period of the day and the second length of the measurement window; or a sixth bin corresponding to the second range of patient step rates and the first period of the day and the second length of the measurement window.

In Example 8, the subject matter of any one or more of Examples 1-7 may optionally be configured such that the first range of patient step rates comprises between 40 and 60 steps per minute and the second range of patient step rates comprises between 60 and 90 steps per minute, and the first period of the day comprises a morning period of the day and the second period of the day comprises an evening period of the day.

In Example 9, the subject matter of any one or more of Examples 1-8 may optionally be configured such that the set of bins correspond to different ranges of patient step rates, comprising: a first bin corresponding to a first range of patient step rates; and a second bin corresponding to a second range of patient step rates higher than the first range, and the assessment circuit is configured to determine the measure of patient weight using the determined measures of patient step force of the first and second bins, with priority to the determined measures of patient step force of the first bin corresponding to the first range of patient step rates lower than the second range of patient step rates.

In Example 10, the subject matter of any one or more of Examples 1-9 may optionally be configured such that the assessment circuit is configured to determine a patient walking speed over the measurement window using the determined patient step rate over the measurement window and to determine the measure of patient weight using the determined patient walking speed and measure of patient step force.

In Example 11, the subject matter of any one or more of Examples 1-10 may optionally be configured such that the medical device comprises an implantable medical device configured to be implanted in a body of the patient, the implantable medical device comprises an accelerometer sensor configured to sense acceleration information of the patient, and the signal receiver circuit is configured to receive the acceleration information from the accelerometer sensor.

In Example 12, the subject matter of any one or more of Examples 1-11 may optionally be configured such that the signal receiver circuit is configured to receive impedance information of the patient and the assessment circuit is configured to determine an indication of patient fluid retention using the received impedance information and the determined measure of patient weight.

In Example 13, the subject matter of any one or more of Examples 1-12 may optionally be configured such that the assessment circuit is configured to receive an indication of patient treatment, and to determine a treatment efficacy using the determined measure of patient weight following treatment.

In Example 14, the subject matter of any one or more of Examples 1-13 may optionally be configured such that the signal receiver circuit is configured to receive heart sound information of the patient and the assessment circuit is configured to determine an indication of heart failure using the received heart sound information and the determined measure of patient weight.

An example (e.g., "Example 15") of subject matter (e.g., a method) may comprise receiving acceleration information of a patient; determining, using an assessment circuit, if a value of the acceleration information exceeds an activity threshold over a measurement window, and, in response to the value of the acceleration information exceeding the activity threshold over the measurement window: detecting patient steps in the measurement window using the acceleration information; determining a patient step rate over the measurement window using the detected patient steps; and determining a measure of patient step force for the measurement window; and determining, using the assessment circuit, a measure of patient weight using the determined patient step rate and measure of patient step force.

In Example 16, the subject matter of Example 15 may optionally be configured to include determining, using the assessment circuit, patient step rates and measures of patient step force for a plurality of respective measurement windows and binning the determined measures of patient step force into one of a set of bins according to the determined patient step rate for the respective measurement window, wherein determining the measure of patient weight comprises using the determined measures of patient step force of one of the set of bins.

In Example 17, the subject matter of any one or more of Examples 1-16 may optionally be configured such that determining patient step rates and measures of patient step force comprises determining patient step rates and measures of patient step force for the plurality of respective measurement windows over a plurality of days, and to include determining daily measures of patient step force for each of the set of bins having determined measures of patient step force for the respective day, wherein determining the measure of patient weight comprises using the determined daily measures of patient step force of one of the set of bins.

In Example 18, the subject matter of any one or more of Examples 1-17 may optionally be configured to include determining, using the assessment circuit, a measure of change of the determined measures of patient step force for one of the set of bins over time, wherein determining the measure of patient weight comprises determining a change in patient weight using the determined measure of change.

In Example 19, the subject matter of any one or more of Examples 1-18 may optionally be configured such that binning the determined measures of patient step force comprises binning the determined measures of patient step force into one of the set of bins according to the determined patient step rate for the respective measurement window and a time-of-day of the measurement window and determining the measure of patient weight comprises using the determined measures of patient step force of one of the set of bins at a specified time-of-day.

In Example 20, the subject matter of any one or more of Examples 1-19 may optionally be configured such that the set of bins correspond to different ranges of patient step rates, comprising a first bin corresponding to a first range of patient step rates and a second bin corresponding to a second range of patient step rates higher than the first range, and determine the measure of patient weight comprises using the determined measures of patient step force of the first and second bins, with priority to the determined measures of patient step force of the first bin corresponding to the first range of patient step rates lower than the second range of patient step rates.

In Example 21, subject matter (e.g., a system or apparatus) may optionally combine any portion or combination of any portion of any one or more of Examples 1-20 to comprise "means for" performing any portion of any one or more of the functions or methods of Examples 1-20, or at least one "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Implantable and ambulatory medical devices frequently contain one or more accelerometer sensors and corresponding processing circuits to determine and monitor patient acceleration information, such as, among other things, cardiac vibration information associated with blood flow or movement in the heart or patient vasculature (e.g., heart sounds, cardiac wall motion, etc.), patient physical activity or position information (e.g., patient posture, activity, etc.), respiration information (e.g., respiration rate, phase, breathing sounds, etc.), etc. The present inventors have recognized, among other things, systems and methods to determine a measure of patient weight using existing implantable or ambulatory medical device sensors, providing additional functionality to existing sensor systems at little to no additional physical cost. The determined measure of patient weight can be used as an additional clinical measure, or as an additional measure in diagnostic algorithms, improving the sensitivity, specificity, confidence, or speed of detection of different patient conditions, determinations, treatment efficacy, or alerts.

Patients exert a force into the earth as they walk. The amplitude of the applied ground force is directly related to patient mass. A patient with a smaller mass exerts a relatively smaller force when walking in contrast to a patient with a larger mass. Existing implantable or ambulatory medical device sensors can detect exerted force during patient movement. However, exerted force during patient movement varies depending on a variety of environmental or patient factors, including the type and speed of patient movement, footwear, gait, surface hardness, fluid retention, time of day, whether the patient is carrying additional objects or weight, moving with the assistance of physical aid or at an artificially fast or slow pace in contrast to a normal moving speed of the patient, etc.

The present inventors have recognized, among other things, that force measurements can be gated using different criteria to provide reliable measures of patient weight. Determined measures of patient weight can be used, in certain examples, to escalate, confirm, verify, or adjust a priority of one or more other patient status determinations or alerts, such as early indications of heart failure, fluid retention, etc., or to determine an improving patient status or treatment efficacy, such as confirming a reduction in patient weight or return to a baseline after diuretics or other heart failure therapy are provided, etc.

Figure 1:
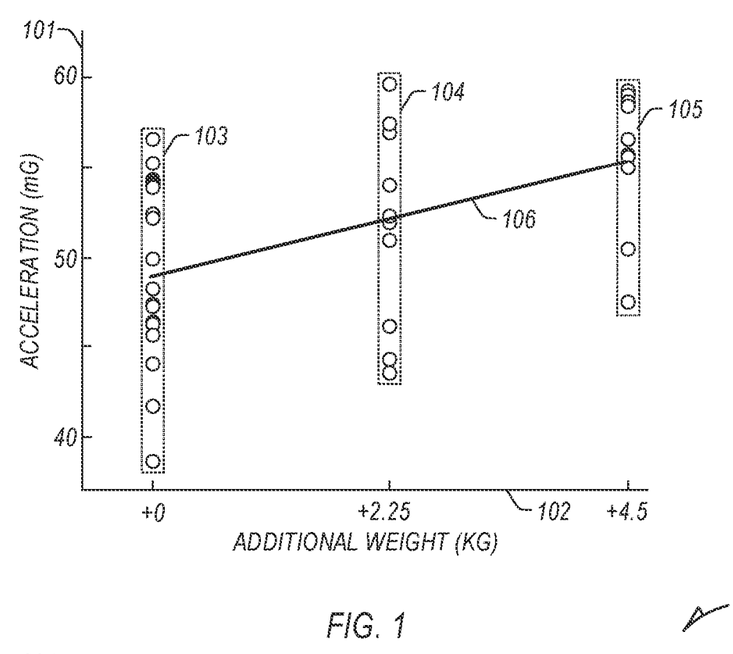
FIGS. 1-2 illustrate relationships between measured patient acceleration information at stable walking speeds with and without additional carried weight.

FIG. 1 illustrates a relationship 100 between measured patient acceleration information 101 in units of milligal (mG) at a stable walking speed with and without additional carried weight 102. A number of 12-second force measurements are illustrated with the patient carrying no additional weight at 103, with the patient carrying an additional +2.25 kg (approximately 5 lbs) at 104, and with the patient carrying an additional +4.5 kg (approximately 10 lbs) at 105. A first line of best fit 106 to the measurements illustrated in FIG. 1 is illustrated having a positive correlation (r) of 0.5.

Figure 2:
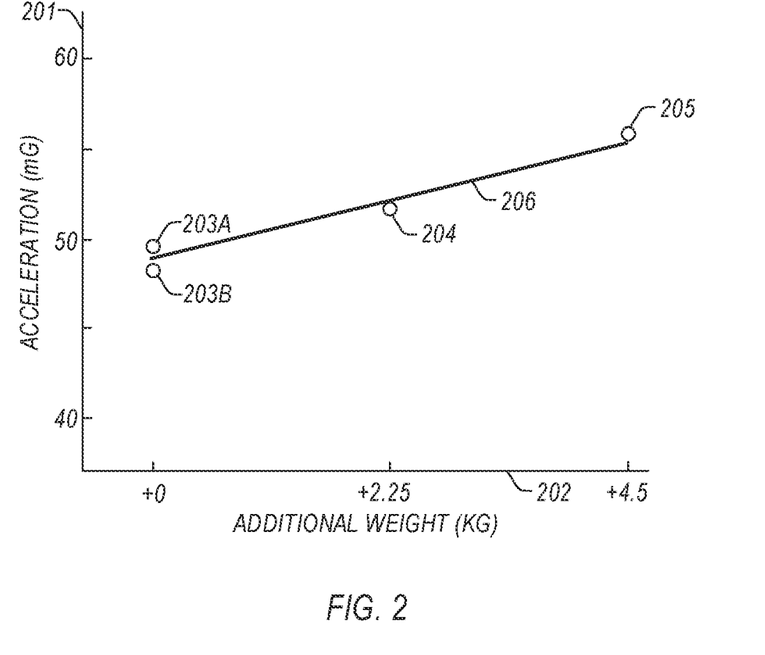

FIG. 2 illustrates a relationship 200 between measured patient acceleration information 201 at a stable walking speed with and without additional carried weight 202. In contrast to the number of 12-second force measurements illustrated in FIG. 1, FIG. 2 illustrates a number of 120-second force measurements with the patient carrying no additional weight at 203A and 203B, with the patient carrying an additional +2.25 kg (approximately 5 lbs) at 204, and with the patient carrying an additional +4.5 kg (approximately 10 lbs) at 205. A second line of best fit 206 to the measurements illustrated in FIG. 2 has a positive correlation (r) of 0.981.

Figure 3:
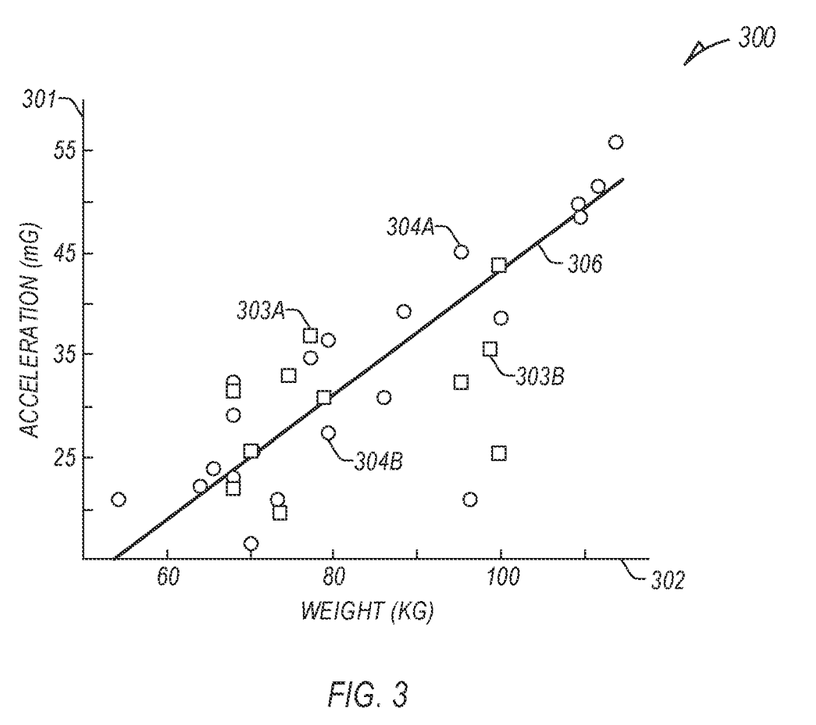
FIG. 3 illustrates a relationship between measured patient acceleration information and patient weight for a number patients moving at different stable walking speeds.

FIG. 3 illustrates a relationship 300 between measured patient acceleration information 301 (e.g., sensor rectified average (SRA) of 120-second force measurements) and patient weight 302 for a number patients moving at walking speeds of 1.0 mph (illustrated using square data points 303A, 303B, etc.) and a number of patients moving at walking speeds of 1.2 mph (illustrated using round data points 304A, 304B, etc.). A third line of best fit 306 illustrates a general relationship between measured force measurements and patient weight. Patient weight determinations can be estimated, for example, along the line of best fit for population data of heart failure patients or patients having implantable or ambulatory medical devices. In other examples, population data can be further separated by other factors, such as age, average moving speed, or otherwise calibrated using other patient input or other indications of physical speed (e.g., GPS watch, estimate of moving speed from mobile phone data, etc.).

Force measurements are generally correlative to patient weight. For example, force measurements collected from different patients from different devices (and different axes of multi-axis devices) at different walking speeds on a treadmill showed moderate correlation (r>0.5) between measured patient acceleration information and patient weight. Average root-means-squared (RMS) values of 120-second period force measurements from a single-axis pulse generator over different walking speeds provided a correlation (r) among the different patients and speeds of 0.54. Average RMS values of 120-second period force measurements from a multi-axis insertable cardiac monitor (ICM) provided different correlations (r) at different axes, with the axis most closely aligning to a vertical axis of the patient providing the highest correlation (r) at 0.56.

In various examples, the same or different accelerometer sensors can be used in overlapping or non-overlapping time periods to determine different patient acceleration information occurring at different frequencies, with different power, processing, performance, or storage requirements. For example, cardiac acceleration information, such as patient heart sounds or endocardial or cardiac acceleration information, or specific patient breath sounds, can occur at a different frequency and require a different, higher sampling rate than patient exertion or activity information, such as patient posture, physical activity, or respiration rate. Patient exertion information is often detected at a sampling rate of 50 Hz or less, whereas heart sound information is often detected at a sampling rate of 200 Hz or higher.

In certain examples, a single acceleration sensor comprising one or more axes (e.g., a single-axis accelerometer, a three-axis accelerometer (e.g., X, Y, and Z axis), etc.) can be gated to require a first sampling rate (e.g., a high sampling rate, such as 200 Hz or higher, etc.) in a first period and a different second sampling rate (e.g., a low sampling rate, such as 50 Hz or lower, etc.) in a second period, non-overlapping with the first period, such as to reduce power consumption of the device. In other examples, different axes of a multi-axis sensor can be sampled at different periods, different sampling rates, or with different processing (e.g., filters, signal conditioning, etc.) or storage requirements. In yet other examples, an implantable or ambulator medical device can include different accelerometer sensors configured to detect different acceleration information of the patient at different periods, different frequencies, or with different processing or storage requirements. For example, it can be advantageous to detect physical activity or exertion information using a more rigid sensor tuned to sense activity having a higher magnitude and lower frequency response than cardiac acceleration information; whereas it can be advantageous to detect cardiac acceleration information using sensor having higher sensitivity and sampling frequency (e.g., a microphone, etc.).

Increasing the amount of collected data in each measurement generally improves the accuracy of measurements and determinations of patient weight. Correlating force measurements to measured patient weight, 12-second force measurements illustrated an error of nearly 3 lbs, whereas 60-second force measurements illustrated an error of approximately 2 lbs, and 120-second force measurements illustrated an error of less than 1 lb. Longer measurement periods (e.g., 120-second periods, such as in contrast to 12-second periods, etc.) provide better determinations of patient weight. As daily variance of 2 lbs can trigger a patient alert, determine measures of patient weight using longer measurement periods can be preferred. Combinations of multiple shorter measurement periods, or combinations of longer and shorter measurement periods can reduce measurement error. However, taking other gating criteria into account (e.g., activity thresholds, step rate, time-of-day, location, etc.), requiring longer measurement periods, in contrast to shorter measurement periods, can reduce the number of separate data measurements available for use each day, a tradeoff.

Patient weight determination, and a confidence of the patient weight determination, can be determined and provided, for example, as a linear or non-linear combination of measurements with respect to preferred grating criteria. Preferred grating criteria can include, among other things, one or more of relatively long measurement periods (e.g., 120-second periods, such as in contrast to relatively shorter measurement periods, etc.), a threshold number of measurements, specified time-of-day, temperature, activity thresholds, step rate, patient moving speed, location, etc.

In certain examples, measurements not meeting each preferred criteria can be used to for the patient weight determination, such as to attain a threshold number of measurements, although decreasing the confidence of the patient weight determination. The threshold number of measurements can be static (e.g., at least two) or dynamic, such as depending on a variation from an expected value. If a single measurement is within a threshold range of an expected (a previous or trending) value, additional measures may not be required. However, if a measurement is outside the threshold range (e.g., ±2 percent of the previous or tending value, ±1 percent of the previous or tending value, etc.), additional measurements can be required. The confidence of the determined measure of patient weight can depend on variation from a previous or trending value, the number of agreeing and preferred criteria making up the determined measure of patient weight, etc. In an example, confidence can be determined using other criteria aside the preferred grating criteria, such as agreement or disagreement with other measurements relatively close in time (e.g., from a single continuous activity period, within a set time, such as within an hour, from the same day, etc.), etc.

In certain examples, measures of patient step force can be determined for the patient using acceleration information sensed during the same time period each day (e.g., in the morning, before noon, between noon and 5 pm, between 5 pm and 10 pm, etc.), such as to reduce patient weight variation associated with food or fluid intake at meals. For many patients, their weight is generally lowest in the morning, peaking with meals, the highest following dinner, and trending downward before and short time after each meal. Measurements taken early in the morning (at first daily patient activity) or late in the morning (before lunch) can be preferred. In other examples, different daily patient weight determinations can be made, such as morning, mid-day, and evening determinations, such as to determine a measure of patient weight fluctuation at relative time periods each day, or to determine an average daily weight using a combination of different daily patient weight determinations. In certain examples, the priority of day-to-day or short term alerts can be reduced for patients having higher intra-day weight variation, such as in contrast to patients having a more stable daily baseline weight with smaller intra-day variation.

A daily patient weight determination can be made as a linear or non-linear combination of force measurements (e.g., with measurements meeting more grating criteria given a larger weight), and daily change measure can be determined, as well as different short-term measurements (e.g., longer than a day but less than one week or two weeks, such as 3 days, 5 days, 1 week, etc.) or long-term measurements (e.g., longer than short-term, such longer than one week, longer than two weeks, etc.). An alert can be triggered or provided based on daily, short, or long-term changes above a threshold, such as indicative of fluid accumulation.

Further gating of force measurements increased correlation. Although an estimate of patient weight can be determined within several percent at relatively high confidence, changes in patient weight detected using a difference in force measurements provide a higher correlation and confidence, with the highest correlation occurring at measurements occurring at the same time and conditions each day, such as to minimize differences in environment, condition, etc. A daily walk, for example, taken with the same footwear, at the same speed, over the same route, at approximately the same time each day, would provide the highest correlation and accuracy. Such activities can be recommended, but as with the weight scales, patient compliance and such measurements are often unreliable. In addition, slower walking speeds (e.g., 1 mph or 1.2 mph, such as in contrast to higher walking speeds, such as 2 mph, etc.) provided better determinations of measures of patient weight.

The present inventors have recognized, among other things, that a repeated signature can be detected to reduce variation in force measurements and improve patient weight determination. In addition to a time of day, force measurements can be gated by activity type, speed, etc. For example, a patient walking up or down a flight of stairs or on an incline or decline can exert different applied ground forces than steps taken on level ground. However, patient step rate on level ground is generally different than patient step rate on stairs, inclines, or declines.

Patient step rates can be detected in patient accelerometer information as repeating patterns of amplitude variations having a relatively constant phase variation throughout a measurement window (e.g., varying less than 30% through the measurement window, etc.) or a threshold amount of the measurement window (e.g., at least 70% of the measurement window, etc.). Walking speed can be determined based on a general relationship with step rate (e.g., assuming 2500 steps per mile for heart failure patients, etc.). Force measurements can be determined for qualifying measurement windows, such as using an average RMS or square-root of the amplitude (SRA) value of the steps over a measurement window, an average amplitude, an amplitude of peak frequency of the measurement window, etc.

Force measurements can be binned by walking speed or step rate, and measurements in specific bins can be used to determine measures of patient weight or changes in measurements in specific bins with time can be used to determine changes in measures of patient weight. In different examples, different numbers of bins having different granularity can be used in steps per minute, miles per hour (mph), or one or more other units. For example, binning by speed, a 1 mph bin can include measurement windows with determined patient walking speed up to 1 mph, a 1.5 mph bin can include measurement windows between 1 mph and 1.5 mph, a 2 mph bin can include measurement windows between 1.5 and 2 mph, etc. In other examples, a 1 mph bin can include measurement windows with determined patient walking speed below 1.5 mph, a 2 mph bin can include measurement windows between 1.5 and 2.5 mph, and a 3 mph bin can include measurement windows above 2.5 mph. In another example, binning by step rates (steps per minute), a first bin can include measurement windows corresponding to a range of patient step rates, such as between 40 and 60 steps per minute, a second bin can include measurement windows corresponding to a second range of patient step rates, such as between 60 and 90 steps per minute, a third bin can include measurement windows corresponding to a third range of patient step rates, such as greater than 90, etc. In other examples, the bins can be more or less granular, having different, higher, lower, or additional ranges.

In certain examples, the step rates or walking speeds themselves can be tracked as an indication of patient health, as a faster step rate or walking speed generally correlates to a better patient status, with an increasing step rate or walking speed indicating an improving patient status and a decreasing step rate or walking speed indicating a worsening patient status.

Figure 4:
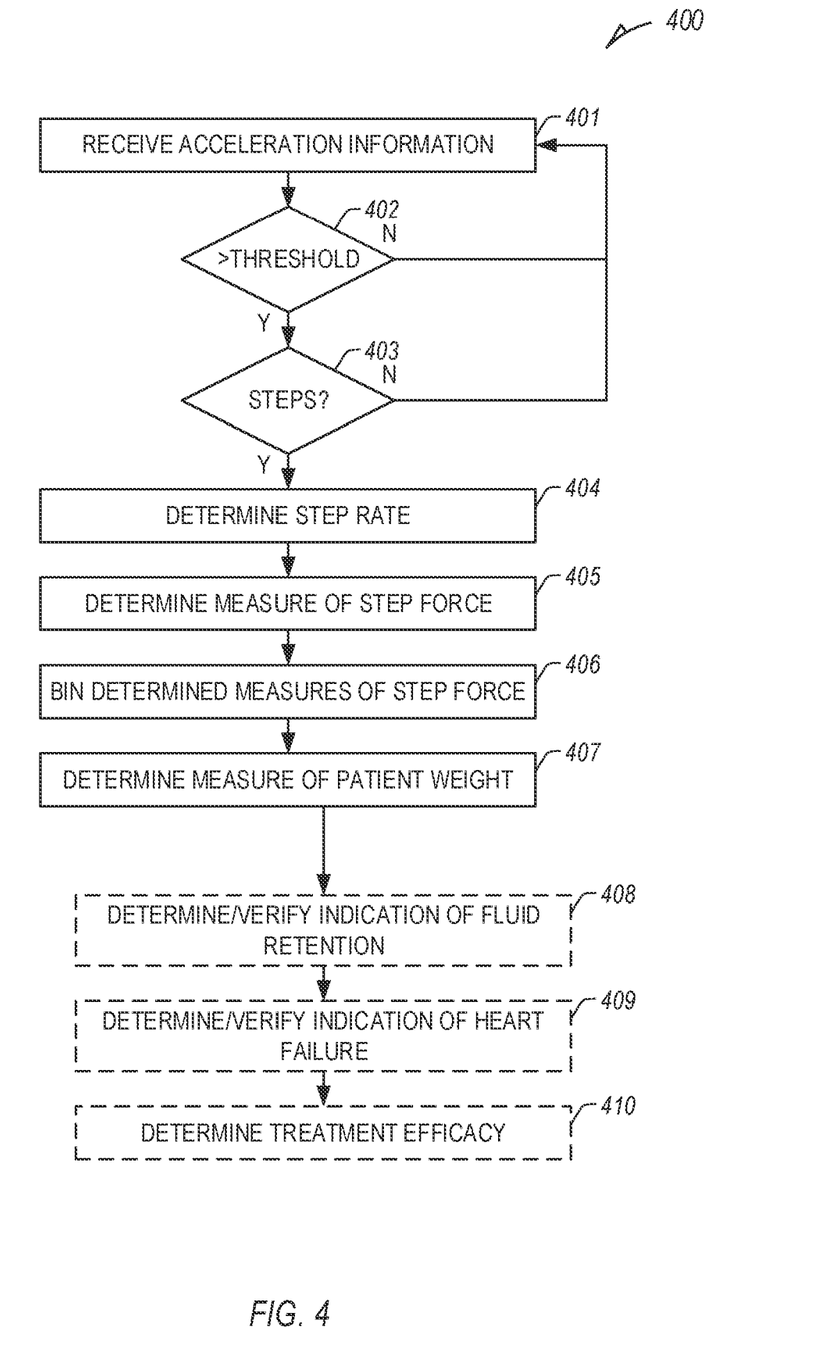
FIG. 4 illustrates an example method of determining a measure of patient weight using patient acceleration information.

FIG. 4 illustrates an example method 400 of determining a measure of patient weight using patient acceleration information. At 401, acceleration information can be received, such as using a signal receiver circuit. In an example, the acceleration information can be sensed using an accelerometer sensor of an implantable medical device. In certain examples, one or both of the accelerometer sensor or the signal receiver circuit can include one or more analog or digital signal processing circuits, such as a filter, rectifier, integrator, etc., configured to condition the sensed acceleration information, and in certain examples, to determine one or more values or measures of the acceleration information. In other examples, the assessment circuit can receive acceleration information from the signal receiver circuit and determine the value of the acceleration information, then compare the determined value to the threshold. The value can include an amplitude or energy measure of the acceleration information representative of a level of patient motion, such as a rate or frequency of peaks across a measurement window, an energy value of the measurement window (e.g., an integrated measure, an RMS value, an SRA value, etc.), etc.

At 402, the value of the acceleration information can be compared to a threshold, such as an activity threshold representative of walking or a level of activity below walking, for example, to quickly filter out periods of time with low or no activity, using an assessment circuit. In an example, the measurement window can a static length or variable depending on the acceleration information (e.g., remaining above the threshold, etc.). In an example, the longer or shorter measurement periods described herein can include a single measurement window, a portion of a measurement window, a combination of sequential full or partial measurement windows, etc. If the value of the acceleration parameter does not exceed the threshold, the method returns to 401. If the value of the acceleration parameter exceeds the threshold, the method continues.

At 403, patient steps can be detected in the acceleration information of the measurement window using the assessment circuit. In an example, the assessment circuit can detect steps using, among other things, one or more of a frequency or amplitude of peaks in the acceleration information, a shape of the acceleration information, repeating patterns of amplitude variations, etc. If patient steps are not detected in the measurement window, the method returns to

401. If patient steps are detected in the measurement window, such as a number of steps above a threshold, or through a threshold portion of the measurement window (e.g., at least 70% of the measurement window, etc.), etc., the method continues.

At 404, a patient step rate can be determined over the measurement window, such as by counting detected steps over the measurement window using the assessment circuit. In an example, the assessment circuit can trip the measurement window to only include portions of the acceleration information having detected steps. In other examples, the assessment circuit can correct missed steps, such as identifying patterns where a step was likely placed (e.g., identifying patterns in sets of patient steps or right/left step variations) but not detected, too much noise or other motion, etc.

In certain examples, the assessment circuit can be configured to determine a patient walking speed using the determined step rate. For example, the determined step rate can be correlated to a population or patient-specific relationship between the determined step rates (for heart failure patients or patients otherwise having implantable or ambulatory medical devices) and patient walking speed. In other examples, the patient step rate can be used instead of a determined walking speed.

At 405, a measure of patient step force can be determined for the measurement window, such as using an RMS, SRA, average peak amplitude, or other measure of the force of the acceleration information over the measurement window using the assessment circuit. In an example, the measure of patient step force can be the same as or different than the value of the acceleration parameter used to determine patient activity above the threshold at 402. For example, the measure of patient step force at 405 can b At 406, the measures of patient step force can be binned into different data sets using the assessment circuit, according to one or more of step rate, walking speed, length of measurement window, time-of-day (e.g., morning, afternoon, evening, or more specific time periods within a day), value of the acceleration parameter, etc. The different bins can represent, in certain examples, different grating criteria. In an example, a daily value of patient step force can be determined for the patient each day, for example, using bins representing preferred grating criteria, filling in or supplementing with other criteria if the preferred grating criteria is absent, light, or otherwise variable or different than an expected value. The measures of patient step force, and corresponding information associated with the one or more different bins, can be stored in memory by the assessment circuit.

At 407, a measure of patient weight can be determined, such as using the measure of patient step force correlated to a population or patient-specific relationship between the measure of patient step force and patient weight. In an example, the assessment circuit can select measures of patient step force from specific bins according to received or predefined preferred grating criteria, and use measures of patient step force from the specific bins to determine the measure of patient weight, such as otherwise described herein.

At 408, an indication of fluid retention can be determined or verified using the assessment circuit, such as a function of the determined measure of patient weight. In certain examples, the assessment circuit can determine one or more indications of fluid retention using physiologic information of the patient, such as impedance, pressure, heart sound, respiration, activity, or other physiologic information of the patient. The determined measure of patient weight can be used to confirm or otherwise improve the confidence or accuracy of the determined indication of fluid retention.

At 409, an indication of heart failure can be determined or verified using the assessment circuit, such as a function of the determined measure of patient weight. In certain examples, the assessment circuit can determine a composite heart failure risk score using physiologic information of the patient, such as impedance, pressure, heart sound, respiration, activity, or other physiologic information of the patient, such as described in one or more of the commonly assigned: Qi An et al., U.S. application Ser. No. 14/510,392, titled "Methods and apparatus for detecting heart failure decompensation event and stratifying the risk of the same"; Robert. J. Sweeney et al., U.S. application Ser. No. 14/282,353, titled "Methods and apparatus for stratifying risk of heart failure decompensation"; Qi An et al. U.S. application Ser. No. 13/726,786, titled "Risk stratification based heart failure detection algorithm", each of which is incorporated herein by reference in their entirety.

Composite heart failure risk scores can detect early indications of heart failure before the patient exhibits physical symptoms, in certain examples, 30 to 60 days before the patient's deteriorating physical status requiring intervention. Patient status often fluctuate, and the time period between threshold crossings of heart failure detection scores can reduce caregiver sensitivity to a slowly-worsening patient status. In contrast, sudden or short-term weight gain, such as 2 lbs over 24-hours, or 5 lbs in a week, is a more immediate (e.g., 3 to 7 days, in contrast to 30 to 60 days) precursor to intervention or hospitalization. Accordingly, a combination of the two measures, the composite heart failure risk score in combination with a determined measure of patient weight, from a single implantable or ambulatory medical device with a single set of sensors, without additional patient compliance issues, can be clinically significant.

At 410, treatment efficacy can be determined, such as using a change in determined measures of patient weight. In an example, a measure of treatment efficacy can be determined from a period of time preceding a request for efficacy (e.g., a current change from a previous day, a short-term trend, etc.). In other examples, the assessment circuit can receive a time of provided therapy to the patient, and determine the measure of treatment efficacy using a change in the determined measure of patient weight after the time of provided therapy. The determined treatment efficacy can provide an indication that a provided therapy, such as in response to an early indication of heart failure, was effective, and whether more or less therapy should be provided in response to the current or future indications.

Figure 5:
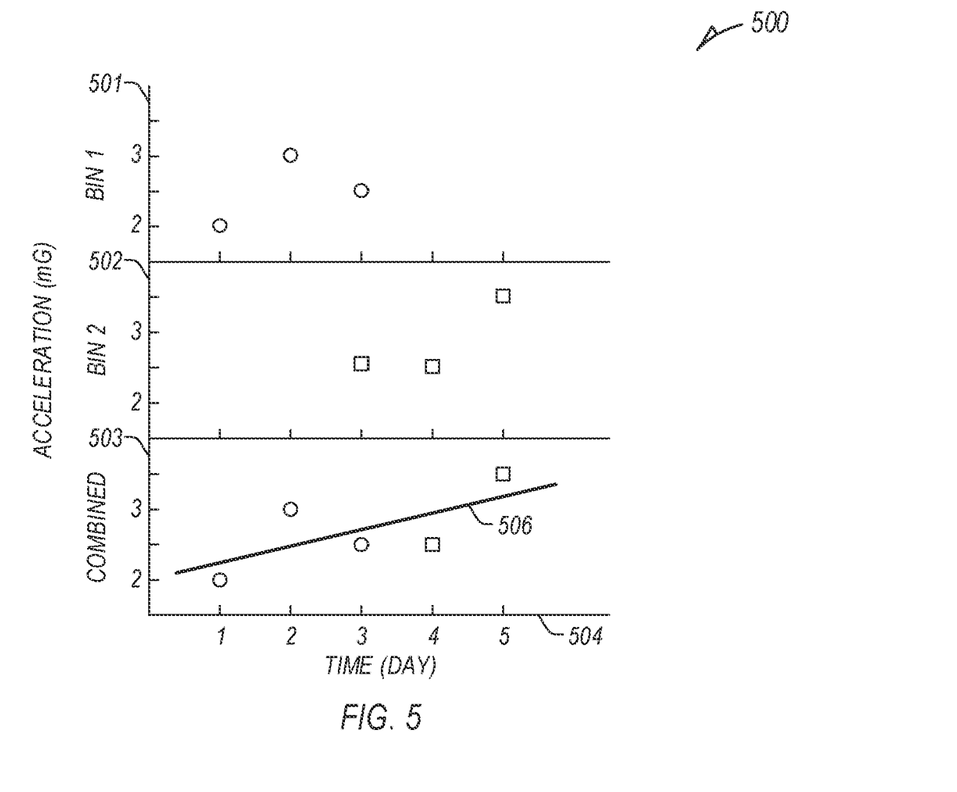
FIG. 5 illustrates a relationship between daily values of patient step force from different bins and a combined daily value of patient step force over a number of days.

FIG. 5 illustrates a relationship 500 between daily values of patient step force from different first and second bins (BIN1, BIN2) 501, 502 and a combined daily value of patient step force 503 over a number of days 504. As described above, the assessment circuit can apply preferred grating criteria to determined measures of patient step force. In this example, the first bin 501 is preferred over the second bin 502, resulting in the combined daily value of patient step force 503 providing a trend 506 of values from the first bin 501 on days 1 through 3, and from the second bin 502 on days 4 and 5, where there are no values in the first bin 501. In other examples, other combinations of values from different bins can be used to determine combined daily values.

Figure 6:
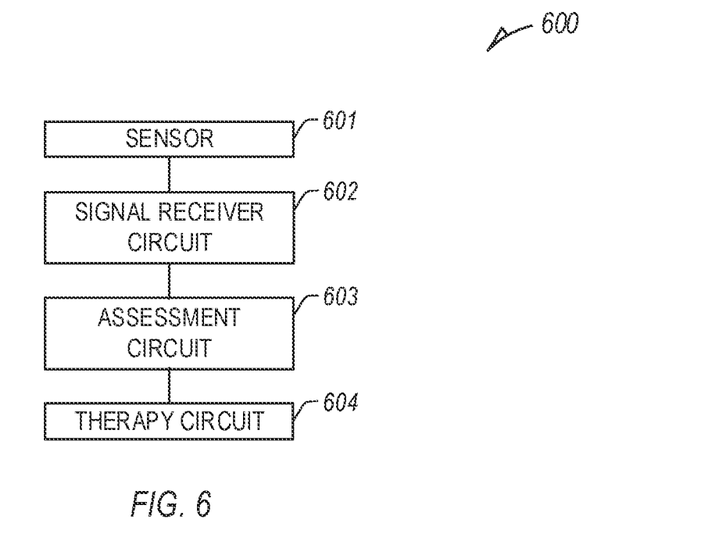
FIG. 6 illustrates an example system to determine measures of patient weight.

FIG. 6 illustrates an example system 600 to determine measures of patient weight, such as a medical-device system, a cardiac rhythm management (CRM) device, etc. In an example, one or more aspects of the example system 600 can be a component of, or communicatively coupled to, an ambulatory medical device (AMD), an insertable cardiac monitor, etc. The system 600 can be configured to monitor, detect, or treat various physiologic conditions of the body, such as cardiac conditions associated with a reduced ability of a heart to sufficiently deliver blood to a body, including heart failure, arrhythmias, dyssynchrony, etc., or one or more other physiologic conditions and, in certain examples, can be configured to provide electrical stimulation or one or more other therapies or treatments to the patient.

The system 600 can include a single medical device or a plurality of medical devices implanted in a patient's body or otherwise positioned on or about the patient to monitor patient physiologic information of the patient using one or more sensors, such as a sensor 601. In an example, the sensor 601 can include one or more of: a respiration sensor configured to receive respiration information (e.g., a respiration rate, a respiration volume (tidal volume), etc.); an acceleration sensor (e.g., an accelerometer, a microphone, etc.) configured to receive cardiac acceleration information (e.g., cardiac vibration information, pressure waveform information, heart sound information, endocardial acceleration information, acceleration information, activity information, posture information, etc.); an impedance sensor (e.g., intrathoracic impedance sensor, transthoracic impedance sensor, etc.) configured to receive impedance information, a cardiac sensor configured to receive cardiac electrical information; an activity sensor configured to receive information about a physical motion (e.g., activity, steps, etc.); a posture sensor configured to receive posture or position information; a pressure sensor configured to receive pressure information; a plethysmograph sensor (e.g., a photoplethysmography sensor, etc.); a chemical sensor (e.g., an electrolyte sensor, a pH sensor, an anion gap sensor, etc.); a temperature sensor; a skin elasticity sensor, or one or more other sensors configured to receive physiologic information of the patient.

The example system 600 can include a signal receiver circuit 602 and an assessment circuit 603. The signal receiver circuit 602 can be configured to receive physiologic information of a patient (or group of patients) from the sensor 601. The assessment circuit 603 can be configured to receive information from the signal receiver circuit 602, and to determine one or more parameters (e.g., physiologic parameters, stratifiers, etc.) or existing or changed patient conditions (e.g., indications of patient dehydration, respiratory condition, cardiac condition (e.g. heart failure, arrhythmia), sleep disordered breathing, etc.) using the received physiologic information, such as described herein. The physiologic information can include, among other things, cardiac electrical information, impedance information, respiration information, heart sound information, activity information, posture information, temperature information, or one or more other types of physiologic information.

The assessment circuit 603 can be configured to provide an output to a user, such as to a display or one or more other user interface, the output including a score, a trend, an alert, or other indication. In other examples, the assessment circuit 603 can be configured to provide an output to another circuit, machine, or process, such as a therapy circuit 604 (e.g., a cardiac resynchronization therapy (CRT) circuit, a chemical therapy circuit, etc.), etc., to control, adjust, or cease a therapy of a medical device, a drug delivery system, etc., or otherwise alter one or more processes or functions of one or more other aspects of a medical-device system, such as one or more cardiac resynchronization therapy parameters, drug delivery, dosage determinations or recommendations, etc. In an example, the therapy circuit 604 can include one or more of a stimulation control circuit, a cardiac stimulation circuit, a neural stimulation circuit, a dosage determination or control circuit, etc. In other examples, the therapy circuit 604 can be controlled by the assessment circuit 603, or one or more other circuits, etc.

Traditional cardiac rhythm management devices, such as insertable cardiac monitors, pacemakers, defibrillators, or cardiac resynchronizers, include implantable or subcutaneous devices having hermetically sealed housings configured to be implanted in a chest of a patient. The cardiac rhythm management device can include one or more leads to position one or more electrodes or other sensors at various locations in or near the heart, such as in one or more of the atria or ventricles of a heart, etc. Accordingly, cardiac rhythm management devices can include aspects located subcutaneously, though proximate the distal skin of the patient, as well as aspects, such as leads or electrodes, located near one or more organs of the patient. Separate from, or in addition to, the one or more electrodes or other sensors of the leads, the cardiac rhythm management device can include one or more electrodes or other sensors (e.g., a pressure sensor, an accelerometer, a gyroscope, a microphone, etc.) powered by a power source in the cardiac rhythm management device. The one or more electrodes or other sensors of the leads, the cardiac rhythm management device, or a combination thereof, can be configured detect physiologic information from the patient, or provide one or more therapies or stimulation to the patient.

Implantable devices can additionally or separately include leadless cardiac pacemakers (LCPs), small (e.g., smaller than traditional implantable cardiac rhythm management devices, in certain examples having a volume of about 1 cc, etc.), self-contained devices including one or more sensors, circuits, or electrodes configured to monitor physiologic information (e.g., heart rate, etc.) from, detect physiologic conditions (e.g., tachycardia) associated with, or provide one or more therapies or stimulation to the heart without traditional lead or implantable cardiac rhythm management device complications (e.g., required incision and pocket, complications associated with lead placement, breakage, or migration, etc.). In certain examples, an leadless cardiac pacemakers can have more limited power and processing capabilities than a traditional cardiac rhythm management device; however, multiple leadless cardiac pacemakers can be implanted in or about the heart to detect physiologic information from, or provide one or more therapies or stimulation to, one or more chambers of the heart. The multiple leadless cardiac pacemaker can communicate between themselves, or one or more other implanted or external devices.

Figure 7:
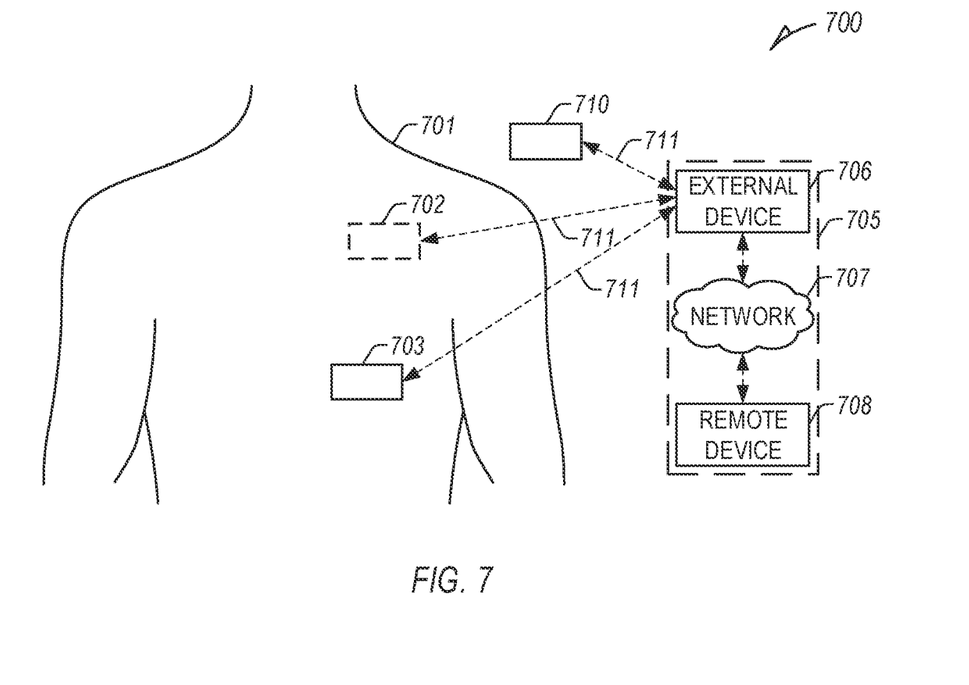
FIG. 7 illustrates an example patient management system and portions of an environment in which the system may operate.

FIG. 7 illustrates an example patient management system 700 and portions of an environment in which the patient management system 700 may operate. The patient management system 700 can perform a range of activities, including remote patient monitoring and diagnosis of a disease condition. Such activities can be performed proximal to a patient 701, such as in a patient home or office, through a centralized server, such as in a hospital, clinic, or physician office, or through a remote workstation, such as a secure wireless mobile computing device.

The patient management system 700 can include one or more ambulatory medical devices, an external system 705, and a communication link 711 providing for communication between the one or more ambulatory medical devices and the external system 705. The one or more ambulatory medical devices can include an implantable medical device (IMD) 702, a wearable medical device 703, or one or more other implantable, leadless, subcutaneous, external, wearable, or ambulatory medical devices configured to monitor, sense, or detect information from, determine physiologic information about, or provide one or more therapies to treat various conditions of the patient 701, such as one or more cardiac or non-cardiac conditions (e.g., dehydration, sleep disordered breathing, etc.).

In an example, the implantable medical device 702 can include one or more traditional cardiac rhythm management devices implanted in a chest of a patient, having a lead system including one or more transvenous, subcutaneous, or non-invasive leads or catheters to position one or more electrodes or other sensors (e.g., a heart sound sensor) in, on, or about a heart or one or more other position in a thorax, abdomen, or neck of the patient 701. In another example, the implantable medical device 702 can include a monitor implanted, for example, subcutaneously in the chest of patient 701, the implantable medical device 702 including a housing containing circuitry and, in certain examples, one or more sensors, such as a temperature sensor, etc.

The implantable medical device 702 can include an assessment circuit configured to detect or determine specific physiologic information of the patient 701, or to determine one or more conditions or provide information or an alert to a user, such as the patient 701 (e.g., a patient), a clinician, or one or more other caregivers or processes. The implantable medical device 702 can alternatively or additionally be configured as a therapeutic device configured to treat one or more medical conditions of the patient 701. The therapy can be delivered to the patient 701 via the lead system and associated electrodes or using one or more other delivery mechanisms. The therapy can include delivery of one or more drugs to the patient 701, such as using the implantable medical device 702 or one or more of the other ambulatory medical devices, etc. In some examples, therapy can include cardiac resynchronization therapy for rectifying dyssynchrony and improving cardiac function in heart failure patients. In other examples, the implantable medical device 702 can include a drug delivery system, such as a drug infusion pump to deliver drugs to the patient for managing arrhythmias or complications from arrhythmias, hypertension, or one or more other physiologic conditions. In other examples, the implantable medical device 702 can include one or more electrodes configured to stimulate the nervous system of the patient or to provide stimulation to the muscles of the patient airway, etc.

The wearable medical device 703 can include one or more wearable or external medical sensors or devices (e.g., automatic external defibrillators (AEDs), Holter monitors, patch-based devices, smart watches, smart accessories, wrist- or finger-worn medical devices, such as a finger-based photoplethysmography sensor, etc.).

The external system 705 can include a dedicated hardware/software system, such as a programmer, a remote server-based patient management system, or alternatively a system defined predominantly by software running on a standard personal computer. The external system 705 can manage the patient 701 through the implantable medical device 702 or one or more other ambulatory medical devices connected to the external system 705 via a communication link 711. In other examples, the implantable medical device 702 can be connected to the wearable medical device 703, or the wearable medical device 703 can be connected to the external system 705, via the communication link 711. This can include, for example, programming the implantable medical device 702 to perform one or more of acquiring physiologic data, performing at least one self-diagnostic test (such as for a device operational status), analyzing the physiologic data, or optionally delivering or adjusting a therapy for the patient 701. Additionally, the external system 705 can send information to, or receive information from, the implantable medical device 702 or the wearable medical device 703 via the communication link 711. Examples of the information can include real-time or stored physiologic data from the patient 701, diagnostic data, such as detection of patient hydration status, hospitalizations, responses to therapies delivered to the patient 701, or device operational status of the implantable medical device 702 or the wearable medical device 703 (e.g., battery status, lead impedance, etc.). The communication link 711 can be an inductive telemetry link, a capacitive telemetry link, or a radio-frequency (RF) telemetry link, or wireless telemetry based on, for example, "strong" Bluetooth or IEEE 802.11 wireless fidelity "Wi-Fi" interfacing standards. Other configurations and combinations of patient data source interfacing are possible.

The external system 705 can include an external device 706 in proximity of the one or more ambulatory medical devices, and a remote device 708 in a location relatively distant from the one or more ambulatory medical devices, in communication with the external device 706 via a communication network 707. Examples of the external device 706 can include a medical device programmer. The remote device 708 can be configured to evaluate collected patient or patient information and provide alert notifications, among other possible functions. In an example, the remote device 708 can include a centralized server acting as a central hub for collected data storage and analysis. The server can be configured as a uni-, multi-, or distributed computing and processing system. The remote device 708 can receive data from multiple patients. The data can be collected by the one or more ambulatory medical devices, among other data acquisition sensors or devices associated with the patient 701. The server can include a memory device to store the data in a patient database. The server can include an alert analyzer circuit to evaluate the collected data to determine if specific alert condition is satisfied. Satisfaction of the alert condition may trigger a generation of alert notifications, such to be provided by one or more human-perceptible user interfaces. In some examples, the alert conditions may alternatively or additionally be evaluated by the one or more ambulatory medical devices, such as the implantable medical device. By way of example, alert notifications can include a Web page update, phone or pager call, E-mail, SMS, text or "Instant" message, as well as a message to the patient and a simultaneous direct notification to emergency services and to the clinician. Other alert notifications are possible. The server can include an alert prioritizer circuit configured to prioritize the alert notifications. For example, an alert of a detected medical event can be prioritized using a similarity metric between the physiologic data associated with the detected medical event to physiologic data associated with the historical alerts.

The remote device 708 may additionally include one or more locally configured clients or remote clients securely connected over the communication network 707 to the server. Examples of the clients can include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 708, including the server and the interconnected clients, may also execute a follow-up scheme by sending follow-up requests to the one or more ambulatory medical devices, or by sending a message or other communication to the patient 701 (e.g., the patient), clinician or authorized third party as a compliance notification.

The communication network 707 can provide wired or wireless interconnectivity. In an example, the communication network 707 can be based on the Transmission Control Protocol/Internet Protocol (TCP/IP) network communication specification, although other types or combinations of networking implementations are possible. Similarly, other network topologies and arrangements are possible.

One or more of the external device 706 or the remote device 708 can output the detected medical events to a system user, such as the patient or a clinician, or to a process including, for example, an instance of a computer program executable in a microprocessor. In an example, the process can include an automated generation of recommendations for anti-arrhythmic therapy, or a recommendation for further diagnostic test or treatment. In an example, the external device 706 or the remote device 708 can include a respective display unit for displaying the physiologic or functional signals, or alerts, alarms, emergency calls, or other forms of warnings to signal the detection of arrhythmias. In some examples, the external system 705 can include an external data processor configured to analyze the physiologic or functional signals received by the one or more ambulatory medical devices, and to confirm or reject the detection of arrhythmias. Computationally intensive algorithms, such as machine-learning algorithms, can be implemented in the external data processor to process the data retrospectively to detect cardia arrhythmias.

Portions of the one or more ambulatory medical devices or the external system 705 can be implemented using hardware, software, firmware, or combinations thereof. Portions of the one or more ambulatory medical devices or the external system 705 can be implemented using an application-specific circuit that can be constructed or configured to perform one or more functions or can be implemented using a general-purpose circuit that can be programmed or otherwise configured to perform one or more functions. Such a general-purpose circuit can include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. "Sensors" can include electronic circuits configured to receive information and provide an electronic output representative of such received information.

The therapy device 710 can be configured to send information to or receive information from one or more of the ambulatory medical devices or the external system 705 using the communication link 711. In an example, the one or more ambulatory medical devices, the external device 706, or the remote device 708 can be configured to control one or more parameters of the therapy device 710. The external system 705 can allow for programming the one or more ambulatory medical devices and can receives information about one or more signals acquired by the one or more ambulatory medical devices, such as can be received via a communication link 711. The external system 705 can include a local external implantable medical device programmer. The external system 705 can include a remote patient management system that can monitor patient status or adjust one or more therapies such as from a remote location.

Figure 8:
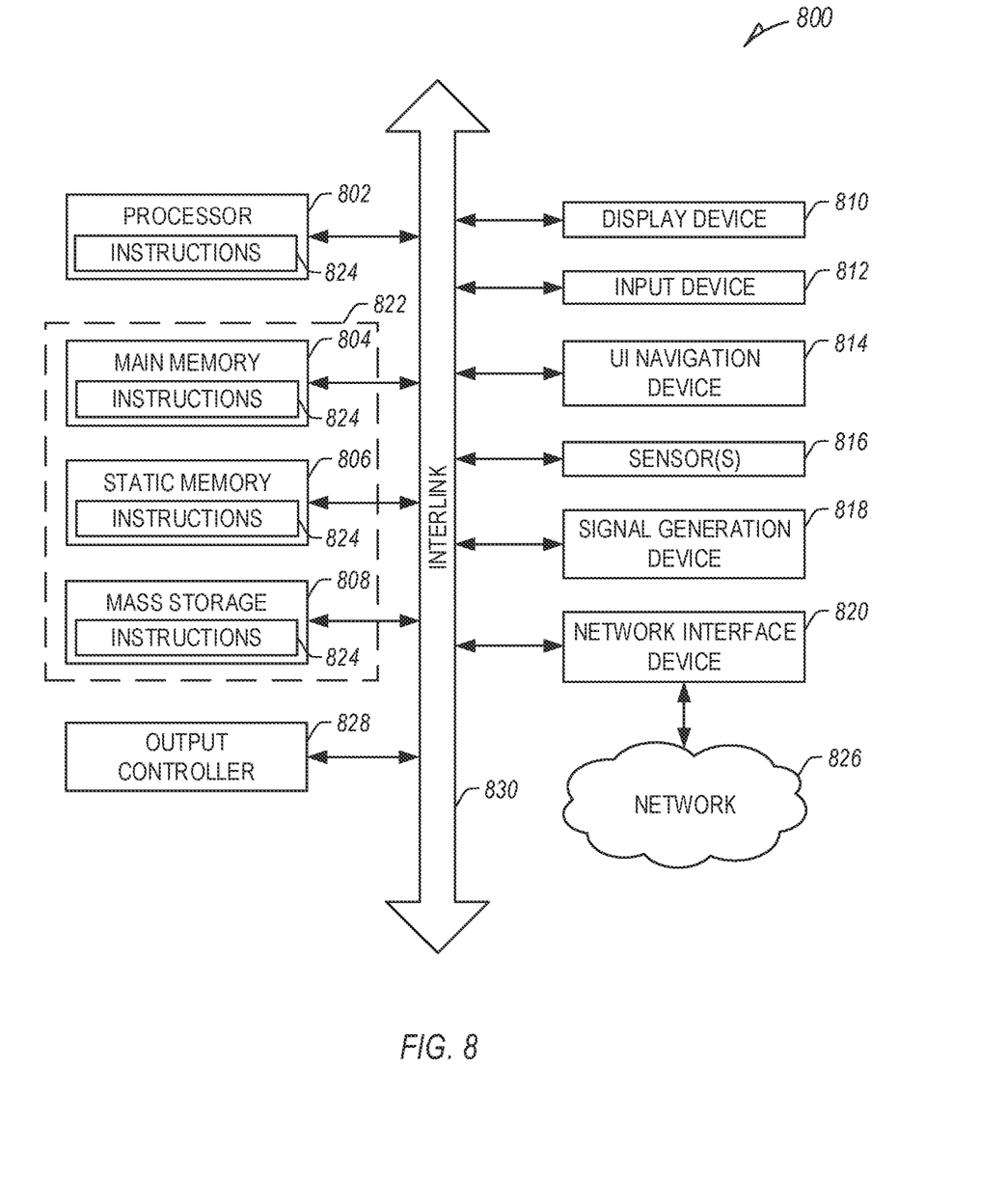
FIG. 8 illustrates a block diagram of an example machine upon which any one or more of the techniques discussed herein may perform.

FIG. 8 illustrates a block diagram of an example machine 800 upon which any one or more of the techniques (e.g., methodologies) discussed herein may perform. Portions of this description may apply to the computing framework of one or more of the medical devices described herein, such as the implantable medical device, the external programmer, etc. Further, as described herein with respect to medical device components, systems, or machines, such may require regulatory-compliance not capable by generic computers, components, or machinery.

Examples, as described herein, may include, or may operate by, logic or a number of components, or mechanisms in the machine 800. Circuitry (e.g., processing circuitry, an assessment circuit, etc.) is a collection of circuits implemented in tangible entities of the machine 800 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 800 follow.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 800 may include a hardware processor 802 (e.g., a central processing unit (CPU), a graphics processing unit (GPU), a hardware processor core, or any combination thereof), a main memory 804, a static memory (e.g., memory or storage for firmware, microcode, a basic-input-output (BIOS), unified extensible firmware interface (UEFI), etc.) 806, and mass storage 808 (e.g., hard drive, tape drive, flash storage, or other block devices) some or all of which may communicate with each other via an interlink (e.g., bus) 830. The machine 800 may further include a display unit 810, an input device 812 (e.g., a keyboard), and a user interface (UI) navigation device 814 (e.g., a mouse). In an example, the display unit 810, input device 812, and UI navigation device 814 may be a touch screen display. The machine 800 may additionally include a signal generation device 818 (e.g., a speaker), a network interface device 820, and one or more sensors 816, such as a global positioning system (GPS) sensor, compass, accelerometer, or one or more other sensors. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the hardware processor 802, the main memory 804, the static memory 806, or the mass storage 808 may be, or include, a machine-readable medium 822 on which is stored one or more sets of data structures or instructions 824 (e.g., software) embodying or utilized by any one or more of the techniques or functions described herein. The instructions 824 may also reside, completely or at least partially, within any of registers of the hardware processor 802, the main memory 804, the static memory 806, or the mass storage 808 during execution thereof by the machine 800. In an example, one or any combination of the hardware processor 802, the main memory 804, the static memory 806, or the mass storage 808 may constitute the machine-readable medium 822. While the machine-readable medium 822 is illustrated as a single medium, the term "machine-readable medium" may include a single medium or multiple media (e.g., a centralized or distributed database, and/or associated caches and servers) configured to store the one or more instructions 824.

The term "machine-readable medium" may include any medium that is capable of storing, encoding, or carrying instructions for execution by the machine 800 and that cause the machine 800 to perform any one or more of the techniques of the present disclosure, or that is capable of storing, encoding, or carrying data structures used by or associated with such instructions. Non-limiting machine-readable medium examples may include solid-state memories, optical media, magnetic media, and signals (e.g., radio frequency signals, other photon-based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 824 may be further transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 800, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A medical device configured to control determination of a measure of patient weight to reduce measurement error, the medical device comprising:
   a signal receiver circuit configured to receive acceleration information of a patient; and
   an assessment circuit configured to determine a value of the acceleration information and, in response to the value of the acceleration information exceeding an activity threshold, to:
   detect patient steps in a measurement window using the acceleration information; and using the detected patient steps:
  determine a patient step rate over the measurement window; and
  determine a measure of patient step force for the measurement window,
wherein the assessment circuit is configured to determine the measure of patient weight using the determined patient step rate and measure of patient step force and to control determination of the measure of patient weight to reduce measurement error.

2. The medical device of claim 1, wherein the assessment circuit is configured to:
  determine patient step rates and measures of patient step force for a plurality of respective measurement windows;
  bin the determined measures of patient step force into one of a set of bins according to the determined patient step rate for the respective measurement window; and
  determine the measure of patient weight using the determined measures of patient step force of at least one of the set of bins.

3. The medical device of claim 2, wherein the assessment circuit is configured to:
  determine patient step rates and measures of patient step force for the plurality of respective measurement windows over a plurality of days;
  determine daily measures of patient step force for each of the set of bins having determined measures of patient step force for a respective day; and
  determine the measure of patient weight using the determined daily measures of patient step force of one of the set of bins.

4. The medical device of claim 2, wherein the measure of patient weight comprises a change in patient weight, and
  wherein the assessment circuit is configured to:
    determine a measure of change of the determined measures of patient step force for one of the set of bins over time; and
    determine the change in patient weight using the determined measure of change.

5. The medical device of claim 4, wherein the assessment circuit is configured to determine at least one of:
  an intra-day change in patient weight using a change in determined measures of patient step force for one of the set of bins occurring over one day;
  a short-term change in patient weight using a change in determined measures of patient step force for one of the set of bins occurring over a first period of time comprising multiple days; or
  a long-term change in patient weight using a change in determined measures of patient step force for one of the set of bins occurring over a second period of time longer than the first period of time.

6. The medical device of claim 2, wherein the assessment circuit is configured to:
  bin the determined measures of patient step force into one of the set of bins according to the determined patient step rate for the respective measurement window and at least one of a time-of-day of the measurement window and a length of the measurement window; and
  determine the measure of patient weight using the determined measures of patient step force of one of the set of bins corresponding to at least one of a specified time-of-day or a specified length of the measurement window.

7. The medical device of claim 6, wherein the set of bins correspond to different ranges of patient step rates and periods of the day, comprising:
  a first bin corresponding to a first range of patient step rates and a first period of the day and a first length of the measurement window; and
  at least one of:
    a second bin corresponding to the first range of patient step rates and the first period of the day and a second length of the measurement window;
    a third bin corresponding to the first range of patient step rates and a second period of the day and the first length of the measurement window;
    a fourth bin corresponding to a second range of patient step rates and the first period of the day and the first length of the measurement window;
    a fifth bin corresponding to the first range of patient step rates and the second period of the day and the second length of the measurement window; or
    a sixth bin corresponding to the second range of patient step rates and the first period of the day and the second length of the measurement window.

8. The medical device of claim 7, wherein the first range of patient step rates comprises between 40 and 60 steps per minute and the second range of patient step rates comprises between 60 and 90 steps per minute, and
  wherein the first period of the day comprises a morning period of the day and the second period of the day comprises an evening period of the day.

9. The medical device of claim 2, wherein the set of bins correspond to different ranges of patient step rates, comprising:
  a first bin corresponding to a first range of patient step rates; and
  a second bin corresponding to a second range of patient step rates higher than the first range, and
  wherein the assessment circuit is configured to determine the measure of patient weight using the determined measures of patient step force of the first and second bins, with priority to the determined measures of patient step force of the first bin corresponding to the first range of patient step rates lower in determination of the measure of patient weight than the second range of patient step rates.

10. The medical device of claim 1, wherein the assessment circuit is configured to:
  determine a patient walking speed over the measurement window using the determined patient step rate over the measurement window; and
  determine the measure of patient weight using the determined patient walking speed and measure of patient step force.

11. The medical device of claim 1, wherein the medical device comprises an implantable medical device configured to be implanted in a body of the patient,
  wherein the implantable medical device comprises an accelerometer sensor configured to sense acceleration information of the patient, and
  wherein the signal receiver circuit is configured to receive the acceleration information from the accelerometer sensor.

12. The medical device of claim 1, wherein the signal receiver circuit is configured to receive impedance information of the patient, and wherein the assessment circuit is configured to determine an indication of patient fluid retention using the received impedance information and the determined measure of patient weight.

13. The medical device of claim 1, wherein the assessment circuit is configured to receive an indication of patient treatment, and to determine a treatment efficacy using the determined measure of patient weight following treatment.

14. The medical device of claim 1, wherein the signal receiver circuit is configured to receive heart sound information of the patient, and
wherein the assessment circuit is configured to determine an indication of heart failure using the received heart sound information and the determined measure of patient weight.

15. A method to control determination of a measure of patient weight to reduce measurement error, the method comprising:
receiving acceleration information of a patient;
determining, using an assessment circuit, a value of the acceleration information over a measurement window and, in response to the value of the acceleration information exceeding an activity threshold over the measurement window:
detecting patient steps in the measurement window using the acceleration information;
determining a patient step rate over the measurement window using the detected patient steps; and
determining a measure of patient step force for the measurement window; and
determining, using the assessment circuit, the measure of patient weight using the determined patient step rate and measure of patient step force and to control determination of the measure of patient weight to reduce measurement error.

16. The method of claim 15, comprising:
determining, using the assessment circuit, patient step rates and measures of patient step force for a plurality of respective measurement windows; and
binning the determined measures of patient step force, using the assessment circuit, into one of a set of bins according to the determined patient step rate for the respective measurement window,
wherein determining the measure of patient weight comprises using the determined measures of patient step force of at least one of the set of bins.

17. The method of claim 16, wherein determining patient step rates and measures of patient step force comprises determining patient step rates and measures of patient step force for the plurality of respective measurement windows over a plurality of days, wherein the method comprises:
determining daily measures of patient step force for each of the set of bins having determined measures of patient step force for a respective day,
wherein determining the measure of patient weight comprises using the determined daily measures of patient step force of one of the set of bins.

18. The method of claim 16, comprising determining, using the assessment circuit, a measure of change of the determined measures of patient step force for one of the set of bins over time,
wherein determining the measure of patient weight comprises determining a change in patient weight using the determined measure of change.

19. The method of claim 16, wherein binning the determined measures of patient step force comprises binning the determined measures of patient step force into one of the set of bins according to the determined patient step rate for the respective measurement window and a time-of-day of the measurement window, and
wherein determining the measure of patient weight comprises using the determined measures of patient step force of one of the set of bins at a specified time-of-day.

20. The method of claim 16, wherein the set of bins correspond to different ranges of patient step rates, comprising:
a first bin corresponding to a first range of patient step rates; and
a second bin corresponding to a second range of patient step rates higher than the first range, and
wherein determining the measure of patient weight comprises using the determined measures of patient step force of the first and second bins, with priority to the determined measures of patient step force of the first bin corresponding to the first range of patient step rates lower in determination of the measure of patient weight than the second range of patient step rates.

* * * * *